United States Patent [19]

Tokuyasu et al.

[11] Patent Number: 5,401,788
[45] Date of Patent: Mar. 28, 1995

[54] ORGANIC PHOSPHORUS COMPOUNDS AND FLAME-RETARDED RESIN COMPOSITIONS CONTAINING THE SAME

[75] Inventors: Noriaki Tokuyasu, Ikoma; Tatsushi Ono; Katsumi Kameda, both of Osaka, all of Japan

[73] Assignee: Daihachi Chemical Industry Co., Ltd., Osaka, Japan

[21] Appl. No.: 208,234

[22] Filed: Mar. 10, 1994

[30] Foreign Application Priority Data

Mar. 16, 1993 [JP] Japan .................................. 5-056107

[51] Int. Cl.$^6$ ...................... C07F 9/6574; C08K 5/527
[52] U.S. Cl. ........................................ 524/119; 558/79
[58] Field of Search ........................ 524/119; 558/79; 523/451, 508

[56] References Cited

U.S. PATENT DOCUMENTS

| | | | |
|---|---|---|---|
| 2,859,086 | 11/1958 | Feild et al. ............................. | 558/79 |
| 2,952,701 | 9/1960 | McConnell et al. .................. | 524/119 |
| 2,974,158 | 3/1961 | Lanham .................................. | 558/79 |
| 3,639,545 | 2/1972 | Wilcox .................................... | 558/79 |
| 4,035,448 | 7/1977 | Mayerhoefer et al. ............. | 524/119 |
| 4,049,617 | 9/1977 | Albright ................................. | 524/119 |
| 4,143,101 | 3/1979 | Mayerhoefer et al. ............. | 524/119 |
| 4,388,431 | 6/1983 | Mauric et al. ........................ | 524/119 |
| 4,458,045 | 7/1984 | Mauric et al. . | |

FOREIGN PATENT DOCUMENTS

| | | |
|---|---|---|
| 961354 | 4/1957 | Germany . |
| 3004184 | 9/1980 | Germany . |
| 49-62424 | 6/1974 | Japan . |
| 62-257949 | 11/1987 | Japan . |
| 80/01697 | 8/1980 | WIPO . |

OTHER PUBLICATIONS

Noda et al.., "Phosphorus–Containing Flame Retardants"; Pap. Fire Retard. Chem. Assoc. [Semi–Annu. Meet] (PFRMDK); 79; (Int. Oppor Fire Retard.: Regul., New Dev., Toxic) pp. 220–246, Mitsui Toatsu Chem. Inc.
Chemical Abstracts vol. 93, citation 133266h.
Kirk–Othmer Encyclopedia of Chem. Tech. vol. 15, pp. 720–721.
Chemistry and Uses of Fire Retardants–J. Lyons (1970 pp. 1, 2.
Kunstoffe (German Plastics) 76 (1986) 10 pp. 943–947.

*Primary Examiner*—Veronica P. Hoke
*Attorney, Agent, or Firm*—Sandler, Greenblum & Bernstein

[57] ABSTRACT

Organic phosphorus compounds of the formula (I):

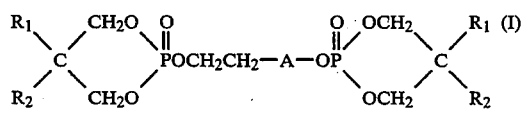

wherein $R_1$ and $R_2$ are, the same or different, a $C_{1-8}$ straight chain or branched chain alkyl group, an optionally substituted $C_{6-12}$ aryl group; and A represents a bond, a lower alkylene group or $-(OCH_2CH_2)_n-$ group, (n is an integer of 1 to 5), which are useful as flame-retardants.

11 Claims, 2 Drawing Sheets

ORGANIC PHOSPHORUS COMPOUNDS AND FLAME-RETARDED RESIN COMPOSITIONS CONTAINING THE SAME

BACKGROUND OF THE INVENTION

1. Field of the Invention

The present invention relates to novel organic phosphorus compounds of non-halogen type and flame-retarded resin compositions containing the same which are excellent in flame-retardant properties and heat resistance.

2. Description of the Related Art

Organic polymers such as thermoplastic resins (e.g., polypropylene, polystyrene and acrylonitrile-butadienestyrene (ABS) resins) and thermosetting resins (e.g., polyurethane and phenol resins) are available at relatively low cost and have excellent properties such as easy molding. Such organic polymers are widely used in all kinds of commodities including electronic components and automobile components. However, these organic polymers are flammable. Once they are involved in fire, they are readily burned and lost. A fire of cable causes great damage to our society. A law has recently been enacted which provides that these organic polymers shall be flame-retardant when used in products for daily use such as electric products, automobile interior decoration components and fiber products. For example, in the United States, there are the UL standards for electric apparatus and MVSS-302 Flame-Retardant Rule for automobiles.

As a known method for giving flame-retardant properties to organic polymers, a flame-retardant is added to organic polymers when preparing a molded product. As the flame-retardants, there are inorganic compounds, organic phosphorus compounds, organic halogen compounds and organic phosphorus compounds containing halogen. Of the above compounds, organic halogen compounds and organic phosphorus compounds containing halogen exhibit excellent flame-retardant effect. However, these compounds containing halogen are pyrolyzed in the process of molding resins and produce hydrogen halide, which corrodes molds and causes resins to be deteriorated and colored. Furthermore, such compounds adversely affect our working environment. Still furthermore, the compounds generate toxic gas, such as hydrogen halide, which is toxic to human bodies.

Typical flame-retardants which do not contain halogens are inorganic compounds such as magnesium hydroxide. However, since these inorganic compounds are inferior in flame-retardant effect, it is necessary to add a large amount to achieve sufficient flame-retardant effect. Thus such flame-retardants have a drawback of allowing resins to be deprived of their inherent properties.

Halogen-free organic phosphorus compounds are generally used as flame-retardant having a relatively favorable flame-retardant effect. Aromatic phosphorus compounds such as triphenyl phosphate (TPP), tricresyl phosphate (TCP) and cresyl diphenylphosphate (CDP), which are typical organic phosphorus compounds, are used as flame retardants for each kind of engineering plastics, such as phenol resin, epoxy resin and polyurethane resin or the like.

However, triphenyl phosphate can hardly give flame-retardant properties to resins because it contains phosphorus at a low ratio. Triphenyl phosphate is usually used together with a halogen type flame-retardant. Furthermore, when triphenyl phosphate is singly used, it must be used in large amounts. This will impair various physical properties of resins and readily cause resins to be colored and deteriorated.

In addition, German Patent No. 3004184C2 discloses compounds of formula (A) as a flame-retardant which is added to an organic polymer such as polyolefin, polypropylene, polystyrene, ABS and polyurethane.

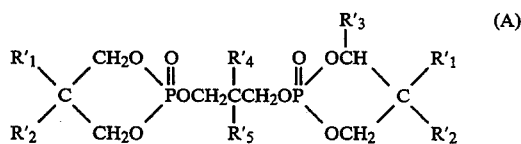

However, one of the main disadvantages of using these compounds lies in that a large amount thereof needs to be added to an organic polymer to give sufficient flame-retardant properties to resins because these compounds contain phosphorus at a low ratio, thereby resulting in inferior physical properties of resins. It is further noted that when $R'_1$ to $R'_5$ in the above formula (A) are methyl groups, the compounds have a low heat resistance, which leads to a disadvantage of causing resins to be colored and deteriorated in the process of molding.

In recent years, the development of plastics having high functional properties, such as engineering plastics and super-engineering plastics are in progress. Since these plastics need a high molding temperature, a flame-retardant is also required to be sufficiently heat resistant. As a known method for improving the heat resistance of flame-retardants, an anti-oxidant such as hindered-phenol compounds, sulfur compounds and amine compounds together with flame-retardant is added to organic polymers. However, even when such anti-oxidants are added to organic polymers, for example, together with the organic phosphorus compounds as mentioned above, coloring of resins cannot be avoided at 200° C. or more.

SUMMARY OF THE INVENTION

The present invention has been made to solve the above drawbacks of the prior art and aims to provide a novel compound which can be used as a flame-retardant for various kinds of resins, having excellent flame-retardant properties and heat resistance and good properties which do not deteriorate or corrode the resins when molded owing to the absence of halogens, and further to provide a flame-retarded resin composition containing the above compound and a resin which is excellent in heat resistance and flame-retardant properties, and can form molded articles without causing dripping of molten resins.

Accordingly, the present invention provides an organic phosphorus compound of the formula (I) (hereinafter referred to as Compound (I)):

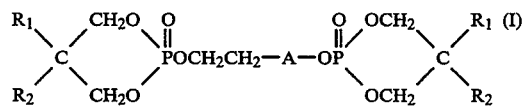

wherein $R_1$ and $R_2$ are, the same or different, a $C_{1-8}$ straight chain or branched chain alkyl group, or an optionally substituted $C_{6-12}$ aryl group; A represents a bond, a lower alkylene group or —$(OCH_2CH_2)_n$— group (n is an integer of 1 to 5) and a flame-retarded resin composition comprising Compound (I) and a resin.

DESCRIPTION OF PREFERRED EMBODIMENTS

Figure 1:
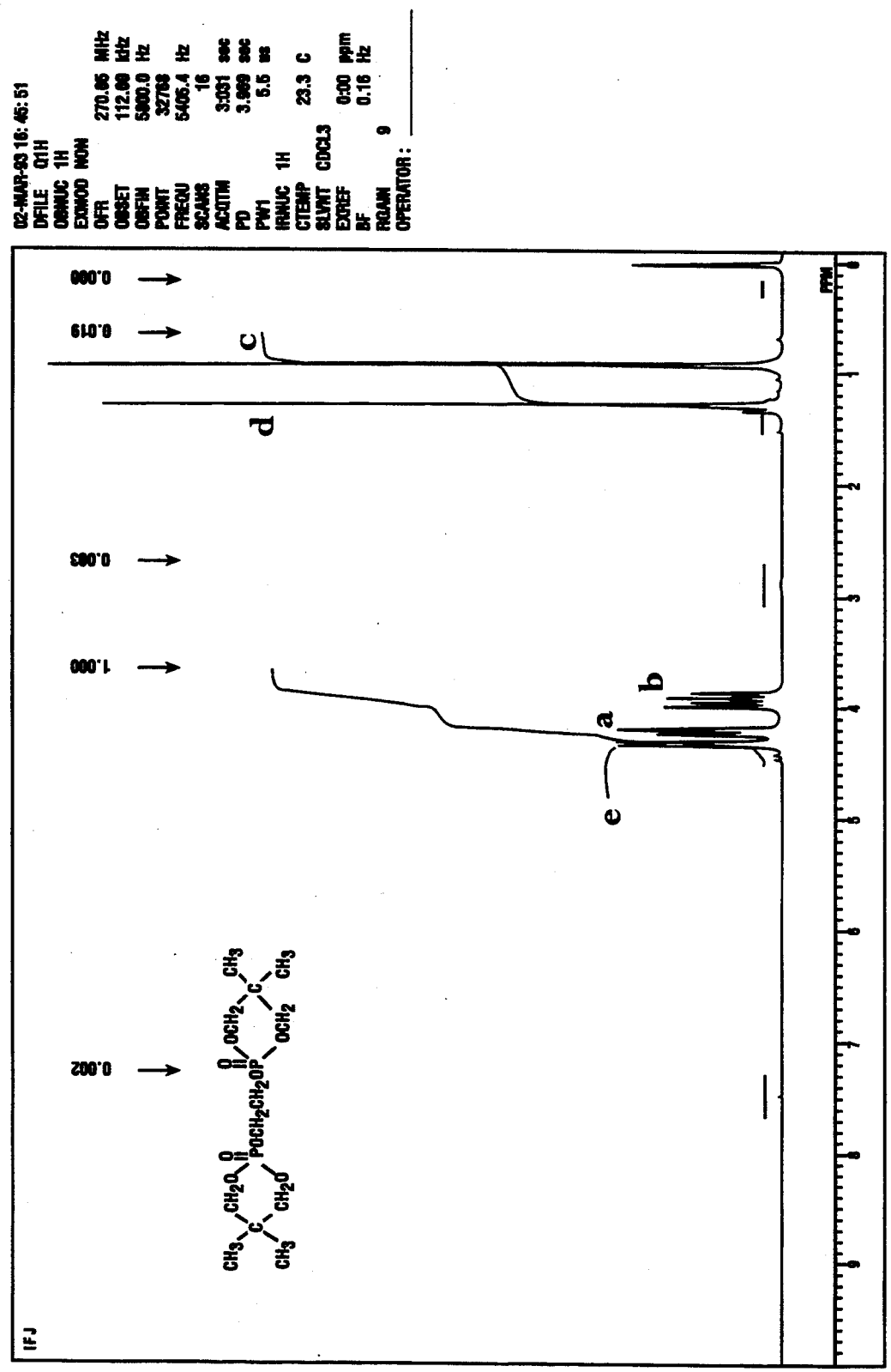
FIG. 1 is an NMR spectrum of Compound 1.

In the above formula (I), examples of the $C_{1-8}$ alkyl groups represented by $R_1$ and $R_2$ include methyl, ethyl, propyl, isopropyl, butyl, isobutyl, pentyl, isopentyl, hexyl, 2-ethylhexyl, n-octyl, and isooctyl groups. In particular, methyl or ethyl groups are preferable.

Examples of the optionally substituted $C_{6-12}$ aryl groups represented by $R_1$ and $R_2$ include phenyl, cresyl, xylyl and naphthyl groups. In particular, phenyl group is preferable.

Such aryl groups may be substituted with one to three $C_{1-3}$ alkyl groups such as methyl, ethyl and propyl.

Examples of the lower alkylene groups represented by A include $C_{1-4}$ alkylene groups such as —$CH_2$—, —$CH_2CH_2$—, and —$CH_2CH_2CH_2$— groups, among which —$CH_2CH_2$— group is preferable.

Examples of —$(OCH_2CH_2)_n$— groups represented by A are —$OCH_2CH_2$— group (n is 1) and —$OCH_2CH_2OCH_2CH_2$— group (n is 2), among which the former is preferable.

Compound (I) of the present invention can be obtained by reacting a compound of the formula (III) (hereinafter referred to as Compound (III)):

(III)

wherein $R_1$ and $R_2$ are as described above and X is a halogen atom, with a compound of the formula (IV) (hereinafter referred to as Compound (IV)):

$$HO(CH_2CH_2O)_nH \qquad (IV)$$

wherein n is as described above for formula (I) or a compound of the formula (V) (hereinafter referred to as Compound (V)):

$$HO(CH_2)_mOH \qquad (V)$$

wherein m is an integer of 2 to 8 in an organic solvent in the presence of an organic base.

In the above reaction, the organic base functions as an acid acceptor. Examples of organic bases include triethylamine, tributylamine, pyridine and dimethylaminopyridine. These bases can be used singly or as a mixture of two or more kinds. The amount of base to be used is 2 to 2.5 moles, preferably 2.05 to 2.2 moles, for one mole of Compound (IV).

The reaction can be conducted in an inert organic solvent such as benzene, toluene, dichloroethane, dioxane or acetonitrile, or the like.

Compound (III) is used in 2 to 2.5 moles, preferably 2 to 2.1 moles, for one mole of Compound (IV).

The reaction can be conducted at 25° to 80° C., preferably 30° to 70° C. for about two to ten hours, preferably about five to seven hours.

The reaction product can be isolated and purified by means of known methods such as solvent extraction, change of acidity or alkalinity, salting out, crystallization and recrystallization.

Of the material compounds used in the process for preparing Compound (I), Compound (III) can be obtained by reacting phosphorus oxyhalide with a diol compound such as neopentyl glycol or the like.

In addition, Compound (IV) is ethylene glycol when n is 1 and diethylene glycol when n is 2. Other examples of Compound (IV) are triethylene glycol and tetraethylene glycol.

Compound (V) is ethylene glycol in case of m being 2, propylene glycol for m being 3 and buthylene glycol for m being 4.

Compound (I) having desired phosphorus content and molecular weight can be prepared by suitably selecting the kinds and amounts of the starting Compounds (III) and (IV) in the above method. The resulting organic phosphorus Compound (I) thus obtained can be used as a flame-retardant singly or as a mixture of two or more kinds.

The flame-retarded resin composition of the present invention comprises a resin and the above organic phosphorus Compound (I) optionally together with an anti-oxidant and other additives. Examples of such additives include halogen type flame-retardants, inorganic flame-retardants, antioxidants, fillers and lubricants.

The kind and amount of Compound (I) to be used is appropriately determined by the degree of flame-retardant properties required therein. The amount of Compound (I) to be used is 0.1 to 100 parts by weight, preferably 5 to 50 parts by weight, for 100 parts by weight of the resin. The resin, the organic phosphorus compound and the above additive, when needed, are headed and molded in accordance with the known method to give a flame-retardant molded article. Compound (I) can be added to monomers to be used in the preparation of a resin with block polymerization, a reaction mixture at the end of the block polymerization, or the resin to be subjected to molding, thereby providing flame-retardant properties thereof.

Examples of the above resins include thermoplastic resins such as chlorinated polyethylene, polyethylene, polypropylene, polybutadiene, polystyrene, impact-resistant polystyrene, polyvinyl chloride, ACS resin, AS resin, ABS resin, polyphenylene oxide, polymethylmetacrylate, polyamide, polyester and polycarbonate; and thermosetting resins such as polyurethane, phenolic resin, melamine resin and urea resin and unsaturated polyester. The above resins may be used singly or as a mixture.

The flame-retarded resin composition of the present invention may contain an anti-oxidant when required. Examples thereof are a hydroquinone compound of the formula (II):

(II)

wherein $R_3$, $R_4$, $R_5$ and $R_6$ are, the same or different, a hydrogen atom or a $C_{1-14}$ straight chain or branched chain alkyl group, and known trivalent organic phosphorus compounds.

Examples of the hydroquinone compounds (II) include hydroquinone, 2,5-di-tert-butylhydroquinone, 2,5-di-tert-amylhydroquinone and octylhydroquinone. Preferred hydroquinone compounds having excellent heat resistance are 2,5-di-tert-amylhydroquinone and 2,5-di-tert-butylhydroquinone.

Examples of the above trivalent organic compounds include triphenylphosphite, tris(nonylphenyl)phosphite, diphenylisodecylphosphite, bis(2,4-di-tert-butylphenyl)pentaerythritoldiphosphite, tetrakis(2,4-tert-butylphenyl)4,4-diphenylenephosphonite.

For such resins as denatured polyphenylene oxide (PPO), polystyrene or ABS resin, Compound (I) can be used together with an inorganic flame-retardant, for example, magnesium hydroxide or antimony trioxide. For polyurethane foam, Compound (I) can be also used together with a non-halogen type compound, such as melamine or urea.

The present invention will be detailed with respect to the following examples which are not intended to be limiting. In the following examples, parts are designated in weights and temperatures in centigrades unless otherwise indicated.

EXAMPLE 1

Into a four necked flask equipped with a stirrer, a thermometer and a condenser with water scrubber was put 104 parts (1 mole) of neopentyl glycol and 100 parts of toluene, followed by addition of 153.5 parts (1 mole) of phosphorus oxychloride at 50° C. in an hour. The reaction was continued for 4 hours to complete dehydrochlorination. To the reaction solution was added 150 g of toluene, to which 31 parts of ethylene glycol (0.5 mole) and 200 parts of dioxane were added at 20° C. and further a mixture of 111 parts of triethylamine and 0.5 part of dimethylaminopyridine was dropwise added at 50° C. for about 2 hours. Then the mixture was raised to 80° C. and maintained for 5 hours to complete the reaction. The precipitated object compound and the amine hydrochloride were collected by filtration and washed with methanol to remove the amine hydrochloride. The residue was dried in vacuo at 100° C. to obtain 155g (yield: 87%) of white powder crystals. The chemical structure of the crystals is as follows (referred to as Compound 1), mp 164° to 166° C.

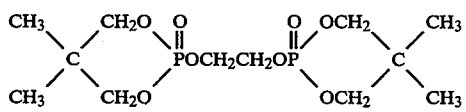

The elemental analysis of Compound 1 ($C_{12}H_{24}O_8P_2$) is shown in Table 1. The NMR spectrum is also shown in FIG. 1.

EXAMPLE 2

White crystalline powders having the following chemical structure (referred to as Compound 2) were prepared in the same manner as Example 1 except that 51 parts of diethylene glycol were used in place of 31 parts of ethylene glycol. The yield was 161 g (80%). mp 116° C.

Figure 2:
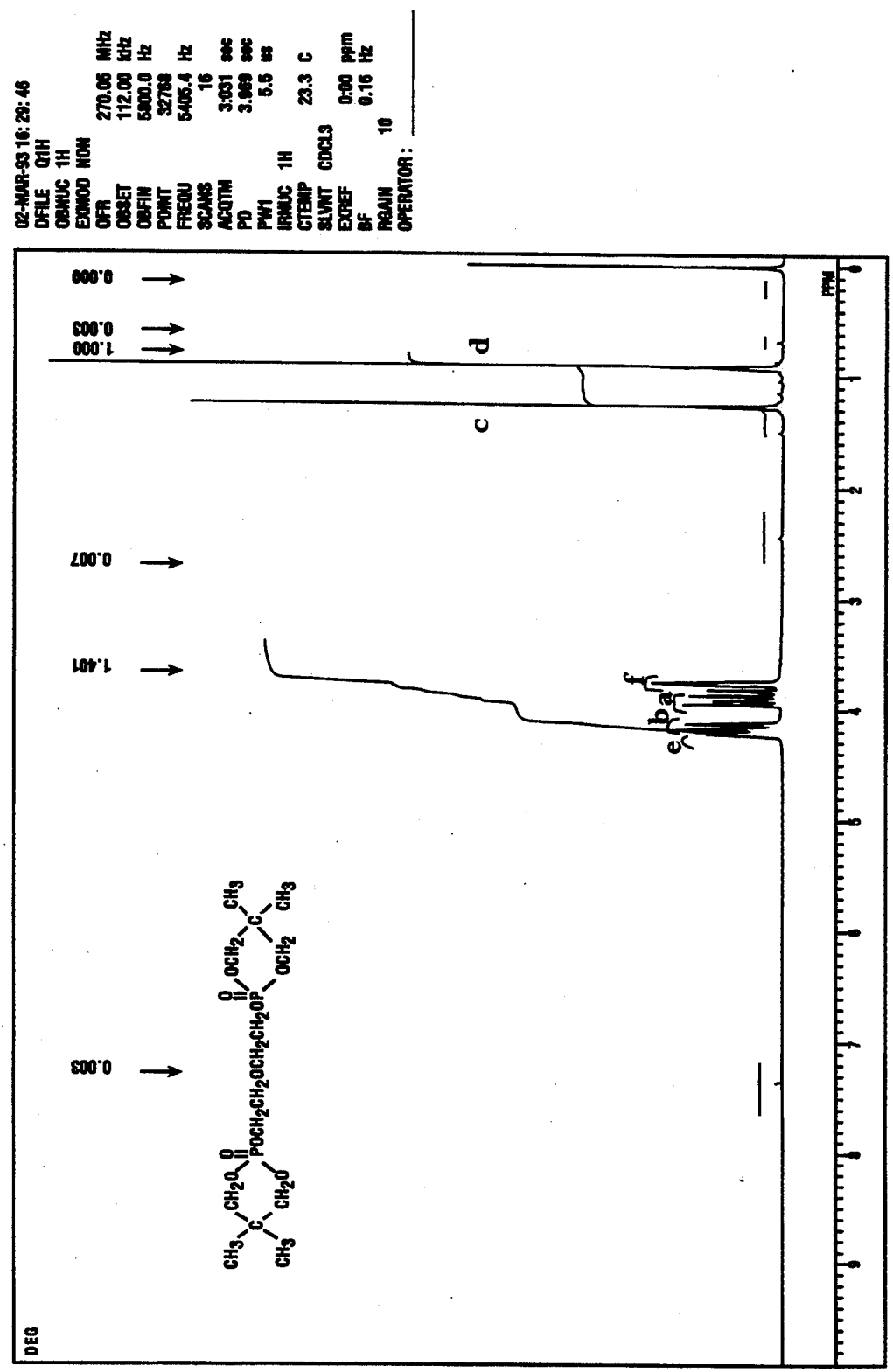
FIG. 2 is an NMR spectrum of Compound 2.

The elemental analysis of Compound 2 ($C_{14}H_{28}O_9P_2$) is shown in Table 1. FIG. 2 shows the NMR spectrum of Compound 2.

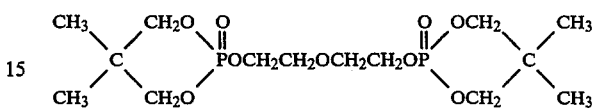

EXAMPLE 3

White crystalline powders having the following structure (referred to as Compound 3) were prepared in the same manner as Example 1 except that 45 parts of 1,4-butanediol was used in place of 31 parts of ethylene glycol. mp 127° C.

The elemental analysis of Compound 3 ($C_{14}H_{28}O_8P_2$) is shown in Table 1.

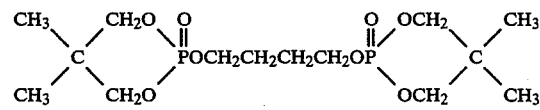

TABLE 1

| Exp. No. | Yield ratio (%) | Melting point (°C.) | Elemental analysis | | | | | | | |
|---|---|---|---|---|---|---|---|---|---|---|
| | | | Theoretical value (%) | | | | Measured value (%) | | | |
| | | | C | H | O | P | C | H | O | P |
| 1 | 87 | 165 | 40.22 | 6.70 | 35.75 | 17.32 | 39.86 | 6.61 | 37.12 | 17.76 |
| 2 | 80 | 116 | 41.79 | 6.97 | 35.82 | 15.42 | 40.86 | 6.52 | 36.24 | 16.08 |
| 3 | 85 | 127 | 43.52 | 7.25 | 33.16 | 16.06 | 42.29 | 7.08 | 25.82 | 16.62 |

Besides, even if the organic phosphorus compounds in accordance with the invention may contain a by-product, such by-product would not affect heat resistance and flame-retardant properties when they are used as a flame-retardant.

The following examples 4 to 6, show the results for performance evaluation on the above Compounds 1 and 2 and the conventional flame-retardant compounds.

Compound A (described in Japanese Unexamined Patent Publication No. 49-62424)

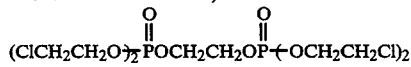

Compound B

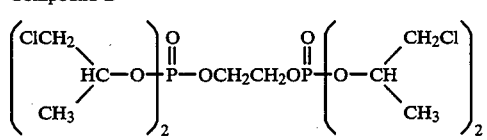

Compound C

Compound D

-continued

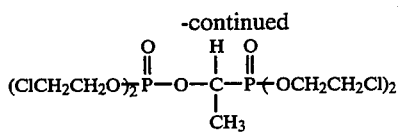

Compound E

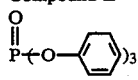

Compound F

EXAMPLE 4

Flame-Retarded Resin Composition

| | |
|---|---|
| Polyol (manufactured by Mitsui Toatsu Chemicals, Inc., Trade name of MN-3050 ONE) | 100 parts |
| Isocyanate (manufactured by Mitsui Toatsu Chemicals, Inc., Trade name of TDI 80/20) | 55.1 parts |
| Polyol silicone oil (manufactured by Nihon Yunika Co., Ltd., Trade name of L-520) | 1.2 parts |
| Tin catalyst | 0.25 part |
| Amine catalyst | 0.15 part |
| Water | 4.5 parts |
| Methylene chloride | 3.0 parts |
| Flame-retardant compound | (predetermined amount shown in Table 1) |

The above ingredients were used to prepare a soft urethane foam in accordance with the one-shot method as follows.

Firstly, the polyol, silicone oil, catalysts, methylene chloride, water and flame-retardant compound were blended and homogenously mixed for a minute with a stirrer of 3000 rpm. Then the isocyanate was added thereto, stirred for 5 to 7 seconds at 3000 rpm and quickly poured into a box with a square-shaped cross section. Immediate foaming occurred to give the maximum volume several minutes later. The product was cured for 30 minutes in a furnace at 120° C. The resulting foam has white and soft open cells.

Each of the resulting foams was cut to obtain a specimen, which was subjected to a burning test using MVSS-302. Furthermore a fresh specimen was treated for 3 minutes in a microwave oven (500 W) followed by heating for 2 hours at 140° C. The specimen was observed for change of color (presence or absence of scorch).

Results are shown in Table 2 and Table 3. In the item "scorch" in Table 3, mark "o" designates almost no change of color while mark "x" is colored in brown.

TABLE 2

| Flame-retardant | (pts.) | Average burning distance (mm) | (pts.) | Average burning distance (mm) | (pts.) | scorch |
|---|---|---|---|---|---|---|
| Compd. 1 | 8 | NB 32.0 | 10 | NB 22.8 | 20 | o |
| Compd. 2 | 8 | NB 37.0 | 10 | NB 26.6 | 20 | o |
| Compd. A | 8 | SE 39.6 | 10 | NB 27.8 | 20 | x |
| Compd. B | 8 | — | 10 | SE 75.9 | 20 | o |
| Compd. C | 8 | SE 76.0 | 10 | SE 52.0 | 20 | o |
| Compd. D | 8 | NB 31.0 | 10 | NB 21.6 | 20 | x |

TABLE 2-continued

| Flame-retardant | (pts.) | Average burning distance (mm) | (pts.) | Average burning distance (mm) | (pts.) | scorch |
|---|---|---|---|---|---|---|
| none | — | burned | | | | o |

NB: Non Burn
SE: Self Extinguish

TABLE 3

| Flame-retardant | (pts.) | scorch |
|---|---|---|
| Compound 1 | 20 | o |
| Compound 2 | 20 | o |
| Compound A | 20 | x |
| Compound B | 20 | o |
| Compound C | 20 | o |
| Compound D | 20 | x |
| none | | o |

As apparent from Table 2 and Table 3, the organic phosphorus compounds of the present invention give better flame-retardant properties and do not occur any scorch, in comparison with the conventional halogen flame-retardant compounds. Even keeping the organic phosphorus compounds of the present invention at 80° C. for 14 days, they did not change the flame-retardant effect.

EXAMPLE 5

To 100 parts of a mixture of impact-resistant polystyrene/PPO resin (45/55) was added 10 parts of the organic phosphorus compound described in Table 4. The mixture was uniformly blended for about 15 minutes using an V type blender with 10 L, and converted into pellets using an extruding machine having internal diameter of 40 mm. A predetermined specimen was prepared from the pellets using a molding machine with a capacity of 4 ounces.

The flame-retardant properties of the specimen were evaluated in accordance with the test method stipulated in UL-94. Five test pieces for each specimen were twice measured for a time from firing to extinguishment. Total times for two measurements are used as burning time and the times are averaged for five test pieces. Then the heat deformation temperature was measured in accordance with D648 in ASTM standard. Juicing phenomena of the surface of the molded article were also determined. Table 4 shows the result thereof.

TABLE 4

| Flame-retardant | Average burning time (sec) | Heat deformation temperature (°C.) | Juicing |
|---|---|---|---|
| Compd. 1 | 35 | 95.2 | none |
| Compd. 2 | 39 | 94.3 | none |
| Compd. E | unextinguished | 81.5 | present |
| Compd. F | 45 | 86.0 | somewhat present |

EXAMPLE 6

To 100 parts of ABS resin (Sebian-V manufactured by Daicel Chemical Industry, Ltd., Japan) was added 10 parts of the organic phosphorus compound described in Table 5, 5 parts of tetrabromobisphenol A, and 2.5 parts of $Sb_2O_3$. The mixture was uniformly stirred for about 15 minutes using a V type blender with 10 L, and converted into pellets using an extruding machine having internal diameter of 40 mm. The pellets were molded into predetermined specimen with a 4 ounce molding machine.

The flame-retardant properties of the specimen were evaluated in accordance with the test method stipulated in UL-94. Five test pieces for each specimen were twice measured for a time from firing to extinguishment. Total times for two measurements are used as burning time and the times are averaged for five test pieces. Then the heat deformation temperature was measured in accordance with D648 in ASTM standard. Juicing phenomena of the surface of the molded article were also determined. Table 5 shows the results thereof.

TABLE 5

| Flame-retardant | Average burning time (sec) | Heat deformation temperature (°C.) | Juicing |
|---|---|---|---|
| Compd. 1 | 7 | 92.0 | none |
| Compd. 2 | 11 | 86.9 | none |
| Compd. E | 20 | 75.3 | present |
| Compd. F | 14 | 80.2 | somewhat present |

The novel organic phosphorus Compound (I) of the present invention, when mixed with various kinds of resins, can impart excellent flame-retardant properties to the resin. The organic phosphorus compounds (I) have low-volatility and excellent heat resistant properties, and are free of causing resin to be colored and deteriorated by pyrolysis in the molding process. Additionally, they hardly impair the physical properties of the resin. In addition, the flame-retarded resin composition can provide a molded product that fails to generate dripping of molded resin when burned.

What is claimed is:

1. An organic phosphorus compound of the formula (I):

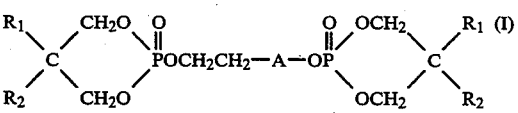

wherein $R_1$ and $R_2$ are, the same or different, a $C_{1-8}$-straight chain or branched chain alkyl group, or an optionally substituted $C_{6-12}$ aryl group; A represents a bond, a lower alkylene group or $-(OCH_2CH_2)_n-$ group; and n is an integer of 1 to 5.

2. The compound of claim 1 in which both of $R_1$ and $R_2$ are methyl group and A is a bond.

3. The compound of claim 1 in which both of $R_1$ and $R_2$ are methyl group and A is $-OCH_2CH_2-$ group.

4. The compound of claim 1 in which both of $R_1$ and $R_2$ are methyl group and A is $-CH_2CH_2-$ group.

5. A flame-retarded resin composition comprising the organic phosphorus compound (I) as defined in claim 1 and a resin.

6. The composition of claim 5 in which the resin is a thermoplastic resin or a thermosetting resin.

7. The composition of claim 5 in which 0.1–100 parts by weight of the organic phosphorus compound (I) are contained for 100 parts by weight of the resin.

8. The composition of claim 7 in which 5–50 parts by weight of the organic phosphorus compound (I) are contained.

9. A flame-retarded resin composition comprising the organic phosphorus compound (I) as defined in claim 2 and a resin.

10. A flame-retarded resin composition comprising the organic phosphorus compound (I) as defined in claim 3 and a resin.

11. A flame-retarded resin composition comprising the organic phosphorus compound (I) as defined in claim 4 and a resin.

* * * * *

UNITED STATES PATENT AND TRADEMARK OFFICE
CERTIFICATE OF CORRECTION

PATENT NO. : 5,401,788
DATED : March 28, 1995
INVENTOR(S) : N. TOKUYASU et al.

It is certified that error appears in the above-indentified patent and that said Letters Patent is hereby corrected as shown below:

On title page , in section [56], "References Cited", " OTHER PUBLICATIONS". line 2, change "al..," to ---al.,---.

On title page , in section [56], "References Cited", " OTHER PUBLICATIONS". line 10, change "(1970" to ---(1970)---.

At column 4, line 38, change "headed" to ---kneaded---.

At column 7. lines 43 and 44, change "cross section" to ---cross-section---.

Signed and Sealed this

Fifteenth Day of October, 1996

Attest:

BRUCE LEHMAN

*Attesting Officer*       *Commissioner of Patents and Trademarks*